(12) United States Patent
Qin et al.

(10) Patent No.: US 6,951,895 B1
(45) Date of Patent: *Oct. 4, 2005

(54) ABSORBENT COMPOSITION

(75) Inventors: Jian Qin, Appleton, WI (US); Palani Raj Ramaswami Wallajapet, Wauwatosa, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/759,108

(22) Filed: Dec. 2, 1996

(51) Int. Cl.[7] .............................................. C08K 3/00
(52) U.S. Cl. ........................... 524/17; 524/27; 524/28; 524/32; 524/35; 524/43; 524/45; 524/47; 524/55; 524/56; 524/57; 524/186; 524/251; 524/394; 524/401; 524/424; 524/425; 524/430; 524/433; 524/436; 524/502; 524/503
(58) Field of Search ............................ 524/32, 56, 556, 524/17, 27, 28, 35, 43, 45, 47, 55, 57, 186, 524/251, 394, 401, 424, 425, 430, 433, 436, 524/502, 503

(56) References Cited

U.S. PATENT DOCUMENTS

| | | |
|---|---|---|
| 2,586,883 A | 2/1952 | Stroh |
| 3,558,744 A | 1/1971 | Michaels et al. |
| 3,669,103 A * | 6/1972 | Harper et al ................. 128/156 |
| 3,794,034 A | 2/1974 | Jones Sr. |
| 3,962,158 A * | 6/1976 | Mima et al .......... 260/17.4 CL |
| 4,104,214 A | 8/1978 | Meierhoefer |
| 4,440,541 A | 4/1984 | Berke ............................. 8/489 |
| 4,454,268 A * | 6/1984 | Otey et al ..................... 524/47 |
| 4,657,537 A | 4/1987 | Zimmerer |
| 4,685,909 A | 8/1987 | Berg et al. |
| 4,818,598 A | 4/1989 | Wong |
| 4,842,593 A | 6/1989 | Jordan et al. |
| 5,011,864 A | 4/1991 | Nielsen et al. ................ 521/70 |
| 5,126,382 A * | 6/1992 | Hollenberg ................... 524/56 |
| 5,364,380 A | 11/1994 | Tanzer et al. |
| 5,461,085 A | 10/1995 | Nagatomo et al. |
| 5,482,843 A | 1/1996 | Brzezinski .................... 435/84 |
| 5,487,895 A | 1/1996 | Dapper et al. ........... 424/278.1 |
| 5,496,933 A | 3/1996 | Kelkenberg ................... 536/20 |
| 5,693,707 A * | 12/1997 | Cheng et al ................. 524/556 |
| 5,807,364 A | 9/1998 | Hansen |
| 5,856,410 A | 1/1999 | Carrico et al. |
| 6,639,120 B1 * | 10/2003 | Wallajapet et al. ......... 604/368 |
| 2003/0125684 A1 | 7/2003 | Qin |
| 2004/0073181 A1 * | 4/2004 | Wallajapet et al. ......... 604/367 |

FOREIGN PATENT DOCUMENTS

| | | |
|---|---|---|
| WO | WO 96/15163 | 5/1996 |
| WO | WO 96/15180 | 5/1996 |
| WO | WO 96/17681 | 6/1996 |

OTHER PUBLICATIONS

U.S. Appl. No. 10/006,781.*
Campbell, Neil A., *Biology*, The Benjamin/Cummings Publishing Company. Inc., 1987 , pp. 45-48 and G-3.
Chang, Raymond, *Chemistry*, Second Edition, Random House. Inc., New York, 1984, pp. 141, 247 & 533.
Lide, David R., Ph, D., Editor, *CRC Handbook of Chemistry & Physics*, 74th Edition, CRC Press, Ann Arbor, Michigan, 1993-1994, pp. 7-1, 7-3, 7-30, 8-17, 8-18, 16-24, 16-25, and 16-26.
Stoll, Vincent S. and John S. Blanchard, "Buffers: Principles and Practice," *Methods in Enzymology: vol. 182, Guide to Protein Purification*, edited by Murray P. Deutscher, Academic Press, Inc., 1990, pp. 24-26.

* cited by examiner

*Primary Examiner*—Bernard Lipman
(74) *Attorney, Agent, or Firm*—Bryan R. Rosiejka (57) ABSTRACT

Disclosed is an absorbent composition comprising each of an acidic and a basic material, wherein the absorbent composition exhibits desirable absorbent properties. Specifically, the present invention relates to an absorbent composition comprising either an acidic water-swellable, water-insoluble polymer having a $pK_a$ between about 2 to about 12 or a basic water-swellable, water-insoluble polymer having a $pK_b$ between about 2 to about 12 and either a basic or an acidic second material. The absorbent composition has the ability to slowly absorb a large quantity of liquid, particularly while under an external pressure. The absorbent composition is useful in disposable absorbent products, such as those disposable absorbent products that are used to absorb bodily liquids.

16 Claims, 1 Drawing Sheet

ABSORBENT COMPOSITION

BACKGROUND OF THE INVENTION

1. Field of the Invention

The present invention relates to an absorbent composition comprising each of an acidic and a basic material, wherein the absorbent composition exhibits desirable absorbent properties. Specifically, the present invention relates to an absorbent composition having the ability to slowly absorb a large quantity of liquid, particularly while under an external pressure. The absorbent composition is useful in disposable absorbent products, such as those disposable absorbent products that are used to absorb bodily liquids.

2. Description of the Related Art

The use of water-swellable, generally water-insoluble absorbent materials, commonly known as superabsorbents, in disposable absorbent personal care products is known. Such absorbent materials are generally employed in absorbent products such as diapers, training pants, adult incontinence products, and feminine care products in order to increase the absorbent capacity of such products while reducing their overall bulk. Such absorbent materials are generally present in absorbent products in a fibrous matrix, such as a matrix of wood pulp fluff. A matrix of wood pulp fluff generally has an absorbent capacity of about 6 grams of liquid per gram of fluff. The superabsorbent materials generally have an absorbent capacity of at least about 10, preferably of about 20, and often of up to 100 times their weight in water. Clearly, incorporation of such absorbent materials in personal care products can reduce the overall bulk while increasing the absorbent capacity of such products.

A wide variety of materials has been described for use as absorbent materials in personal care products. Such materials include natural-based materials such as agar, pectin, gums, carboxyalkyl starch, and carboxyalkyl cellulose, as well as synthetic materials such as polyacrylates, polyacrylamides, and hydrolyzed polyacrylonitrile. While such natural-based absorbent materials are known for use in personal care products, they have not gained wide usage in such products. The natural-based absorbent materials have not gained wide usage in personal care products, at least in part, because their absorbent properties are generally inferior compared to the synthetic absorbent materials, such as the sodium polyacrylates. Specifically, many of the natural-based materials tend to form soft, gelatinous masses when swollen with a liquid. When employed in absorbent products, the presence of such soft gelatinous masses tends to prevent the transport of liquid within the fibrous matrix in which the absorbent materials are incorporated. This phenomenon is known as gel-blocking. Once gel-blocking occurs, subsequent insults of liquid cannot be efficiently absorbed by the product, and the product tends to leak. Further, many of the natural-based materials exhibit poor absorption properties, particularly when subjected to external pressures.

In contrast, the synthetic absorbent materials are often capable of absorbing large quantities of liquid while maintaining a generally stiff, non-mucilaginous character. Accordingly, the synthetic absorbent materials can be incorporated in absorbent products while minimizing the likelihood of gel-blocking.

One property of currently available superabsorbent materials is that such materials typically very rapidly absorb the liquid that comes into contact with the superabsorbent material. While such quick absorbency of the liquid may be desirable in many applications, there are certain applications in which it is not desirable. For example, in an absorbent structure that is insulted with a liquid at only a very localized location, it would generally be desirable to have the liquid distributed throughout the entire volume of the absorbent structure so that the absorbent capacity of the entire absorbent structure is utilized. However, if the superabsorbent material located near the localized insult location absorbs the liquid very quickly, such superabsorbent material may swell and block the flow of the liquid throughout the rest of the absorbent structure, possibly resulting in the liquid leaking out of the absorbent structure in the area of the localized insult location. As such, it may be desirable to employ a superabsorbent material in the localized insult location that actually absorbs the liquid at a slow rate. This would allow the liquid to be distributed throughout the absorbent structure first and then be subsequently absorbed by the slowly-absorbing superabsorbent material.

Several methods are known to slow down the liquid absorbing rate of a relatively fast-rate-absorbing superabsorbent material. For example, it is possible to coat the fast-rate-absorbing superabsorbent material with a material that is nonabsorbent and/or hydrophobic. Such coating materials tend to temporarily shield the underlying superabsorbent material from any liquid and, thus, delay the absorption of the liquid by the superabsorbent material. However, such coating materials often reduce the overall liquid capacity of the superabsorbent material, add to the expense and complexity of preparing the superabsorbent material, and may negatively affect other liquid handling properties of the superabsorbent material.

It is, therefore, an object of the present invention to provide an absorbent composition that absorbs a liquid at a relatively slower rate but with about the same final capacity as compared to commercially available synthetic, superabsorbent materials.

It is also an object of the present invention to provide an absorbent composition that may be prepared from natural-based materials since such may reduce the overall cost of preparing the absorbent composition as well as providing for additional beneficial properties of the absorbent composition such as biodegradability or compostability.

It is also an object of the present invention to provide an absorbent composition that may be prepared simply and with a minimum of materials and additives so as to reduce the overall cost of preparing the absorbent composition as well as reduce the potential deleterious effect that such additives might have on the overall absorbent properties of the absorbent composition.

It is also an object of the present invention to provide an absorbent composition that exhibits unique properties so that such absorbent composition may be used in novel applications.

SUMMARY OF THE INVENTION

In one aspect, the present invention concerns an absorbent composition that absorbs liquid at a relatively slow rate but which is still able to absorb a relatively large quantity of the liquid, even when the absorbent composition is absorbing the liquid under an external pressure.

One embodiment of the present invention concerns an absorbent composition comprising a mixture of:

a) an acidic water-swellable, water-insoluble polymer having a $pK_a$ between about 2 to about 12; and b) a basic material;

wherein the absorbent composition exhibits a Free Swell value that is at least about 15 grams per gram of absorbent composition and a Time to Reach 60 Percent of Free Swell Capacity value of at least about 5 minutes.

Another embodiment of the present invention concerns an absorbent composition comprising a mixture of:
  a) a basic water-swellable, water-insoluble polymer having a $pK_b$ between about 2 to about 12; and
  b) an acidic material;

wherein the absorbent composition exhibits a Free Swell value that is at least about 15 grams per gram of absorbent composition and a Time to Reach 60 Percent of Free Swell Capacity value of at least about 5 minutes.

In another aspect, the present invention concerns a process for preparing an absorbent composition that exhibits desired absorbent properties.

In one embodiment of the present invention, a process for preparing an absorbent composition comprises mixing together:
  a) an acidic water-swellable, water-insoluble polymer having a $pK_a$ between about 2 to about 12; and
  b) a basic material;

wherein the prepared absorbent composition exhibits a Free Swell value that is at least about 15 grams per gram of absorbent composition and a Time to Reach 60 Percent of Free Swell Capacity value of at least about 5 minutes.

In another embodiment of the present invention, a process for preparing an absorbent composition comprises mixing together:
  a) a basic water-swellable, water-insoluble polymer having a $pK_b$ between about 2 to about 12; and
  b) an acidic material;

wherein the prepared absorbent composition exhibits a Free Swell value that is at least about 15 grams per gram of absorbent composition and a Time to Reach 60 Percent of Free Swell Capacity value of at least about 5 minutes.

In another aspect, the present invention concerns a disposable absorbent product comprising an absorbent composition of the present invention that exhibits desired absorbent properties.

In one embodiment of the present invention, a disposable absorbent product comprises a liquid-permeable topsheet, a backsheet attached to the topsheet, and an absorbent structure positioned between the topsheet and the backsheet wherein the absorbent structure comprises an absorbent composition of the pr sent invention.

DETAILED DESCRIPTION OF THE PREFERRED EMBODIMENTS

It has now been discovered that an absorbent composition may be prepared that exhibits a relatively high total liquid absorption capacity as well as a relatively slow liquid absorbing rate. In accordance with this invention, the absorbent composition may be prepared by mixing together an acidic material and a basic material, wherein each of the acidic and basic materials has specific properties, and the absorbent composition exhibits significant and unexpected improvements in its absorbent properties, including improved total liquid absorption as well as a slower liquid absorbing rate, as compared to the properties exhibited by either the acidic or basic materials alone.

The absorbent composition of the present invention generally comprises two essential, but different, materials. The first material is a water-swellable, water-insoluble polymer. As used in the absorbent composition of the present invention, the water-swellable, water-insoluble polymer to a large extent needs to provide the absorbent composition with its liquid-absorbing capacity. As such, the water-swellable, water-insoluble polymer needs to be effective to provide a desired amount of liquid-absorbing capacity to the absorbent composition.

As used herein, the term "water-swellable, water-insoluble" is meant to refer to a material that, when exposed to an excess of water, swells to its equilibrium volume but does not dissolve into the solution. As such, a water-swellable, water-insoluble material generally retains its original identity or physical structure, but in a highly expanded state, during the absorption of the water and, thus, must have sufficient physical integrity to resist flow and fusion with neighboring particles.

As used herein, a material will be considered to be water soluble when it substantially dissolves in excess water to form a solution, thereby losing its initial, typically particulate, form and becoming essentially molecularly dispersed throughout the water solution. As a general rule, a water-soluble material will be free from a substantial degree of crosslinking, as crosslinking tends to render a material water insoluble.

One property of the water-swellable, water-insoluble polymer which is relevant to its effectiveness in providing a desired amount of liquid-absorbing capacity to the absorbent composition is its molecular weight. In general, a water-swellable, water-insoluble polymer with a higher molecular weight will exhibit a higher liquid-absorbing capacity as compared to a water-swellable, water-insoluble polymer with a lower molecular weight.

The water-swellable, water-insoluble polymer useful in the absorbent composition may generally have a wide range of molecular weights. A water-swellable, water-insoluble polymer having a relatively high molecular weight is often beneficial for use in the present invention. Nonetheless, a wide range of molecular weights is generally suitable for use in the present invention. Water-swellable, water-insoluble polymers suitable for use in the present invention will beneficially have a weight average molecular weight greater than about 100,000, more beneficially greater than about 200,000, suitably greater than about 500,000, more suitably greater than about 1,000,000, and up to about 10,000,000. Methods for determining the molecular weight of a polymer are generally well-known in the art.

It is sometimes more convenient to express the molecular weight of a polymer in terms of its viscosity in a 1.0 weight percent aqueous solution at 25° C. Polymers suitable for use in the present invention will suitably have a viscosity in a 1.0 weight percent aqueous solution at 25° C. of from about 100 centipoise (100 mPa·s) to about 80,000 centipoise (80,000 mPa·s), more suitably from about 500 centipoise (500 mPa·s) to about 80,000 centipoise (80,000 mPa·s), and most suitably from about 1,000 centipoise (1,000 mPa·s) to about 80,000 centipoise (80,000 mPa·s).

The water-swellable, water-insoluble polymer useful in the absorbent composition will generally be crosslinked. The amount of crosslinking should generally be above a minimum amount sufficient to make the polymer water-insoluble but also below some maximum amount so as to allow the polymer to be sufficiently water swellable so that the water-swellable, water-insoluble polymer absorbs a desired amount of liquid.

Crosslinking of the polymer may generally be achieved by either of two different types of crosslinking agents. The first type of crosslinking agent is a polymerizable crosslinking agent. Suitable polymerizable crosslinking agents are generally reactive to the monomer or monomers used to prepare the polymer and, thus, generally comprise at least two functional groups that are capable of reacting with the monomers. Examples of suitable polymerizable crosslinking agents include ethylenically unsaturated monomers, such as N,N'-methylene bis-acrylamide, for free radical polymerization and polyamines or polyols for condensation polymerization.

The second type of crosslinking agent is a latent crosslinking agent. Latent crosslinking agents generally do not take part in the overall polymerization process but, instead, are reactive to the polymer at a later point in time when a proper crosslinking condition is provided. Suitable post treatment conditions include using heat treatment, such as a temperature above about 60° C., exposure to ultraviolet light, exposure to microwaves, steam or high humidity treatment, high pressure treatment, or treatment with an organic solvent.

Latent crosslinking agents suitable for use in the present invention are generally water soluble. A suitable latent crosslinking agent is an organic compound having at least two functional groups or functionalities capable of reacting with any carboxyl, carboxylic, amino, or hydroxyl groups on the polymer. Examples of suitable latent crosslinking agents include, but are not limited to, diamines, polyamines, diols, polyols, polycarboxylic acids, and polyoxides. Another suitable latent crosslinking agent comprises a metal ion with more than two positive charges, such as $Al^{3+}$, $Fe^{3+}$, $Ce^{3+}$, $Ce^{4+}$, $Ti^{4+}$, $Zr^{4+}$, and $Cr^{3+}$.

When the polymer is a cationic polymer, a suitable crosslinking agent is a polyanionic material such as sodium polyacrylate, carboxymethyl cellulose, or polyphosphate.

The water-swellable, water-insoluble polymer useful in the absorbent composition will either be acidic or basic in nature. As used herein, an "acidic" material is intended to refer to a material that may act as an electron acceptor. In general, acidic, water-swellable, water-insoluble polymers useful in the absorbent composition will be weakly acidic in nature. As such, acidic, water-swellable, water-insoluble polymers useful in the absorbent composition will beneficially have a $pK_a$ between about 2 to about 12, more beneficially between about 2 to about 10, and suitably between about 3 to about 6. It may sometimes be more convenient to measure the pH of the monomer or monomers used to prepare a polymer. Although the pH of the monomer or monomers and the polymer prepared from such monomers may not be identical, such pH values should be substantially similar. As such, acidic, water-swellable, water-insoluble polymers useful in the absorbent composition will be prepared from monomers that beneficially have a $pK_a$ between about 2 to about 12, more beneficially between about 2 to about 10, and suitably between about 3 to about 6. If a polymer is prepared from two or more monomers, each of the monomers used should beneficially have a $pK_a$ between about 2 to about 12, more beneficially between about 2 to about 10, and suitably between about 3 to about 6, although insubstantial amounts of monomers having a $pK_a$ less than about 2 or greater than about 12 may be used as long as such monomers do not negatively affect the desired properties of the water-swellable, water-insoluble polymer useful herein.

The use of acidic, water-swellable, water-insoluble polymers that are strongly acidic, exhibiting a $pK_a$ less than about 2, have been found to result in absorbent compositions that generally do not exhibit the desired slow-rate of absorbing liquids. The use of acidic, water-swellable, water-insoluble polymers that are too weakly acidic, exhibiting a $pK_a$ greater than about 12, have generally been found to result in absorbent compositions that generally do not exhibit the desired liquid absorbent capacity. The $pK_a$ of an acid represents the extent of dissociation of or, in other words, the strength of the acid and is intended herein to be measured at the conditions, such as at a specific temperature, under which the water-swellable, water-insoluble polymer is being used. Suitably, the $pK_a$ is measured at about 25° C. In general, the weaker the acid, the higher the $pK_a$ value will be. The $pK_a$ values for many acids at various temperatures are well known and may be found in any of many available references, such as in the CRC Handbook of Chemistry & Physics, $75^{th}$ Edition, edited by David R. Lide, CRC Press (1994).

Suitable weakly acidic, water-swellable, water-insoluble polymers will include functional groups that are capable of acting as weak acids. Such functional groups include, but are not limited to, carboxyl groups, sulphate groups, sulfite groups, and phosphate groups. Suitably, the functional groups are carboxyl groups. Generally, the functional groups are attached to a crosslinked base polymer. Suitable base polymers include polyacrylamides, polyvinyl alcohols, ethylene maleic anhydride copolymer, polyvinylethers, polyacrylic acids, polyvinylpyrrolidones, polyvinylmorpholines, and copolymers thereof. Natural based polysaccharide polymers may also be used and include carboxymethyl celluloses, carboxymethyl starchs, hydroxypropyl celluloses, algins, alginates, carrageenans, acrylic grafted starchs, acrylic grafted celluloses, and copolymers thereof. Synthetic polypeptides can also be used such as polyaspartic acid and polyglutamic acid.

The acidic, water-swellable, water-insoluble polymer generally needs to be in its free acid form. In general, it is desired that the acidic, water-swellable, water-insoluble polymer beneficially have at least about 50 molar percent, more beneficially at least about 70 molar percent, suitably at least about 80 molar percent, more suitably at least about 90 molar percent, and most suitably substantially about 100 molar percent of its acidic functional groups in free acid form. Alternatively, then, the acidic, water-swellable, water-insoluble polymer should not be substantially neutralized when used in the absorbent composition of the present invention. In general, it is desired that the acidic, water-swellable, water-insoluble polymer have a degree of neutralization of its acidic functional groups that is beneficially less than about 50 molar percent, more beneficially less than about 30 molar percent, suitably less than about 20 molar percent, more suitably less than about 10 molar percent, and most suitably substantially about 0 molar percent.

As used herein, a "basic" material is intended to refer to a material that may act as an electron donor. In general, basic, water-swellable, water-insoluble polymers useful in the absorbent composition will be weakly basic in nature. As such, basic, water-swellable, water-insoluble polymers useful in the absorbent composition will beneficially have a $pK_b$ between about 2 to about 12, more beneficially between about 2 to about 10, and suitably between about 3 to about 6. It may sometimes be more convenient to measure the pH of the monomer or monomers used to prepare a polymer.

Although the pH of the monomer or monomers and the polymer prepared from such monomer or monomers may not be identical, such pH values should be substantially similar. As such, basic, water-swellable, water-insoluble polymers useful in the absorbent composition will be prepared from monomers that beneficially have a $pK_b$ between about 2 to about 12, more beneficially between about 2 to about 10, and suitably between about 3 to about 6. If a polymer is prepared from two or more monomers, each of the monomers used should beneficially have a $pK_b$ between about 2 to about 12, more beneficially between about 2 to about 10, and suitably between about 3 to about 6, although insubstantial amounts of monomers having a $pK_b$ less than about 2 or greater than about 12 may be used as long as such monomers do not negatively affect the desired properties of the water-swellable, water-insoluble polymer useful herein.

The use of basic, water-swellable, water-insoluble polymers that are strongly basic, exhibiting a $pK_b$ less than about 2, have been found to result in absorbent compositions that generally do not exhibit the desired slow-rate of absorbing liquids. The use of basic, water-swellable, water-insoluble polymers that are too weakly basic, exhibiting a $pK_b$ greater than about 12, have generally been found to result in absorbent compositions that generally do not exhibit the desired liquid absorbent capacity. The $pK_b$ of a base represents the extent of dissociation of or, in other words, the strength of the base and is intended herein to be measured at the conditions, such as at a specific temperature, under which the water-swellable, water-insoluble polymer is being used. Suitably, the $pK_b$ is measured at about 25° C. In general, the weaker the base, the higher the $pK_b$ value will be. The $pK_b$ values for bases at various temperatures are well known and may be found in any of many available references, such as in the CRC Handbook of Chemistry & Physics, 75$^{th}$ Edition, edited by David R. Lide, CRC Press (1994).

Suitable weakly basic, water-swellable, water-insoluble polymers will include functional groups that are capable of acting as weak bases. Such functional groups include, but are not limited to, primary, secondary, or tertiary amino groups, imino groups, imido groups, and amido groups. Suitably the functional groups are amino groups. Generally, the functional groups are attached to a crosslinked base polymer. Suitable base polymers include polyamines, polyethyleneimines, polyacrylamides, and polyquaternary ammoniums, and copolymers thereof. Natural based polysaccharide polymers may also be used and include chitin and chitosan. Synthetic polypeptides can also be used such as polyasparagins, polyglutamines, polylysines, and polyarginines.

The basic, water-swellable, water-insoluble polymer generally needs to be in its free base form. In general, it is desired that the basic, water-swellable, water-insoluble polymer beneficially have at least about 50 molar percent, more beneficially at least about 70 molar percent, suitably at least about 80 molar percent, more suitably at least about 90 molar percent, and most suitably substantially about 100 molar percent of its basic functional groups in free base form. Alternatively, then, the basic, water-swellable, water-insoluble polymer should not be substantially neutralized when used in the absorbent composition of the present invention. In general, it is desired that the basic, water-swellable, water-insoluble polymer have a degree of neutralization of its basic functional groups that is beneficially less than about 50 molar percent, more beneficially less than about 30 molar percent, suitably less than about 20 molar percent, more suitably less than about 10 molar percent, and most suitably substantially about 0 molar percent.

The acidic or basic water-swellable, water-insoluble polymer may generally be used in the absorbent composition in a variety of forms. Examples of forms that the acidic or basic water-swellable, water-insoluble polymer may take include particles, flakes, fibers, films, and nonwoven structures. When the absorbent composition is used in absorbent disposable products, it is generally desired that the acidic or basic water-swellable, water-insoluble polymer be in the form of discrete particles, fibers, or flakes. When in the form of a particle, it is generally desired that the particle have a maximum cross-sectional dimension beneficially within the range from about 50 micrometers to about 2,000 micrometers, suitably within the range from about 100 micrometers to about 1,000 micrometers, and more suitably within the range from about 300 micrometers to about 600 micrometers.

Commercially available superabsorbents are generally in a substantially neutralized or salt form. This is because, in general, in order to have a relatively high capacity for liquid absorption, a water-swellable, water-insoluble polymer must be a polyelectrolyte. However, as discussed herein, the acidic or basic water-swellable, water-insoluble polymers useful in the present invention are substantially in their free acid or free base form, respectively. Furthermore, since the acidic or basic functionality, respectively, of such water-swellable, water-insoluble polymers useful herein are relatively weak in nature, such weakly acidic or basic functionalities do not readily dissociate when placed in a liquid such as water or an aqueous sodium chloride solution. Therefore, such weakly acidic or basic water-swellable, water-insoluble polymers in their free acid or free base form, respectively, generally do not have, on their own, a relatively high capacity for liquid absorption.

It has been discovered in the present invention, however, that when such an acidic or basic water-swellable, water-insoluble polymer, substantially in its free acid or free base form, respectively, is mixed with a basic second material or an acidic second material, respectively, the resulting absorbent composition will exhibit both a relatively high capacity for liquid absorption as well as a relatively slow liquid absorbing rate. This is believed to be because as the mixture is placed in an aqueous solution, the acidic or basic water-swellable, water-insoluble polymer, substantially in its free acid or free base form, respectively, reacts with the basic second material or the acidic second material, respectively, and the chemical equilibrium is in favor of converting the acidic or basic water-swellable, water-insoluble polymer from its free acid or free base form, respectively, to its respective salt form. As such, the mixture comprising the converted water-swellable, water-insoluble polymer will now exhibit a relatively high capacity for liquid absorption. However, because the conversion of the water-swellable, water-insoluble polymer, from its free acid or free base form, respectively, to its respective salt form is a relatively slow process of ionization and ion diffusion into the polymer, the water-swellable, water-insoluble polymer will also exhibit a relatively slow liquid absorbing rate. In addition, the conversion of the water-swellable, water-insoluble polymer, from its free acid or free base form, respectively, to its respective salt form in an electrolyte-containing solution, such as an aqueous sodium chloride solution, has a substantial desalting effect on the electrolyte-containing solution, thereby improving the liquid-absorbing performance of the mixture comprising the water-swellable, water-insoluble polymer by alleviating the salt-poisoning effect.

In contrast to the above, it has been found that a single material or polymer, comprising both acidic and basic functional groups within its molecular structure, will not exhibit the desired absorbent properties described herein. This is believed to be because such acidic and basic functional groups within a single molecular structure will typically react with each other and might result in an over-crosslinked polymer structure. As such, it generally is not possible to prepare the absorbent composition of the present invention by preparing a copolymer from acidic and basic monomers or by preparing a molecular level dispersion, such as in an aqueous solution, of water-soluble acidic and basic materials since during such copolymerization or molecular level dispersion the acidic and basic materials will typically react with each other and crosslink.

In one embodiment of the present invention, then, the absorbent composition will comprise a mixture of a weakly acidic water-swellable, water-insoluble polymer, substantially in its free acid form, and a basic second material. Examples of suitable basic second materials include, but are not limited to, polymeric basic materials such as polyamines, polyimines, polyamides, polyquatery ammoniums, chitins, chitosans, polyasparagins, polyglutamines, polylysines, and polyarginines; organic basic materials such as organic salts and aliphatic and aromatic amines, imines, and amides; and inorganic bases such as metallic oxides, such as aluminum oxide; hydroxides, such as barium hydroxide; salts such as calcium carbonate; and mixtures thereof. The basic second material can generally be either a strong or a weak base. However, the strength of the basicity of the basic second material has been found to affect the liquid absorption rate of the absorbent composition. Generally, an absorbent composition comprising a relatively stronger basic second material will exhibit a relatively faster liquid absorption rate as compared to an absorbent composition comprising a relatively weaker basic second material.

In one beneficial embodiment of the present invention, the basic second material can also suitably be a water-swellable, water-insoluble polymer. In such an embodiment, both the acidic water-swellable, water-insoluble polymer and the basic, water-swellable, water-insoluble polymeric second material can be used to contribute to the total liquid absorptive capacity of the absorbent composition, thereby achieving on overall higher liquid absorptive capacity of the absorbent composition as compared to the use of a basic second material that is not a water-swellable, water-insoluble polymer. However, it has been found that when the basic second material is a water-swellable, water-insoluble polymer, it is generally desired that such a basic, water-swellable, water-insoluble polymeric second material beneficially has a $pK_b$ between about 2 to about 12, more beneficially between about 2 to about 10, and suitably between about 3 to about 6. The use of a basic, water-swellable, water-insoluble polymeric second material that is strongly basic, exhibiting a $pK_b$ less than about 2, has been found to result in absorbent compositions that generally do not exhibit the desired slow-rate of absorbing liquids.

In another embodiment of the present invention, the absorbent composition will comprise a mixture of a weakly basic water-swellable, water-insoluble polymer, substantially in its free basic form, and an acidic second material. Examples of suitable acidic second materials include, but are not limited to, polymeric acidic materials such as polyacrylic acid, polymaleic acid, carboxymethyl cellulose, alginic acid, polyaspartic acid, and polyglutamic acid; organic acidic materials such as aliphatic and aromatic acids; and inorganic acids such as metallic oxides, such as aluminum oxide; and salts such as iron chloride. The acidic second material can generally be either a strong or a weak acid. However, the strength of the acidity of the acidic second material has been found to affect the liquid absorption rate of the absorbent composition. Generally, an absorbent composition comprising a relatively stronger acidic second material will exhibit a relatively faster liquid absorption rate as compared to an absorbent composition comprising a relatively weaker acidic second material.

In one beneficial embodiment of the present invention, the acidic second material can also suitably be a water-swellable, water-insoluble polymer. In such an embodiment, both the basic water-swellable, water-insoluble polymer and the acidic, water-swellable, water-insoluble polymeric second material can be used to contribute to the total liquid absorptive capacity of the absorbent composition, thereby achieving on overall higher liquid absorptive capacity of the absorbent composition as compared to the use of an acidic second material that is not a water-swellable, water-insoluble polymer. However, it has been found that when the acidic second material is a water-swellable, water-insoluble polymer, it is generally desired that such an acidic, water-swellable, water-insoluble polymeric second material beneficially has a $pK_a$ between about 2 to about 12, more beneficially between about 2 to about 10, and suitably between about 3 to about 6. The use of an acidic, water-swellable, water-insoluble polymeric second material that is strongly acidic, exhibiting a $pK_a$ less than about 2, has been found to result in absorbent compositions that generally do not exhibit the desired slow-rate of absorbing liquids.

The basic or acidic second material may generally be used in the absorbent composition in a variety of forms. Examples of forms that the basic or acidic second material may take include particles, flakes, fibers, films, and nonwoven structures. When the absorbent composition is used in absorbent disposable products, it is generally desired that the basic or acidic second material be in the form of discrete particles, fibers, or flakes. When in the form of a particle, it is generally desired that the particle have a maximum cross-sectional dimension beneficially within the range from about 50 micrometers to about 2,000 micrometers, suitably within the range from about 100 micrometers to about 1,000 micrometers, and more suitably within the range from about 300 micrometers to about 600 micrometers. The absorbent composition may also be in the form of bicomponent fibers, wherein one component is the polymer and the other component is the second material. Such a bicomponent fiber may be a side-by-side bicomponent fiber or a sheath-and-core bicomponent fiber. Such bicomponent fibers may be prepared by known methods, such as co-extrusion methods.

In general, the acidic or basic water-swellable, water-insoluble polymer, substantially in its free acid or free base form, respectively, is mixed with a basic second material or an acidic second material, respectively, in the absorbent composition in a molar ratio of the respective acidic and basic functionalities that is sufficient to provide the absorbent composition with desired absorbent properties. The molar ratio of the acidic or basic water-swellable, water-insoluble polymer, respectively, to the basic second material or the acidic second material is beneficially from about 10:1 to about 1:10, suitably from about 4:1 to about 1:4, more suitably from about 2:1 to about 1:2, and most suitably at about 1:1.

The absorbent composition of the present invention suitably has the ability to absorb a liquid, herein referred to as Free Swell (FS). The method by which the Free Swell value is determined is set forth below in connection with the examples. The Free Swell values determined as set forth below and reported herein refer to the amount in grams of an aqueous solution, containing 0.9 weight percent sodium chloride, a gram of a material can absorb in about 10 hours under a negligible load of about 0.01 pound per square inch (psi). As a general rule, it is desired that the absorbent composition of the present invention has an initial Free Swell value, for a load of about 0.01 psi, of at least about 15, beneficially of at least about 20, suitably of at least about 25, and up to about 200 grams per gram. As used herein, the term "initial Free Swell value" is meant to refer to that Free Swell value exhibited by a material as measured within about one day after preparation of the material while the material is stored at ambient conditions, such as at about 24° C. and between about 30 to about 60 percent relative humidity.

The absorbent composition of the present invention also suitably has the ability to absorb a liquid while the absorbent composition is under an external pressure or load, herein referred to as Absorbency Under Load (AUL). Synthetic polymeric materials, such as sodium polyacrylates, having a generally high ability to absorb a liquid while under a load, have been found to minimize the occurrence of gel-blocking when incorporated in absorbent products. The method by which the Absorbency Under Load is determined is set forth below in connection with the examples. The Absorbency Under Load values determined as set forth below and reported herein refer to the amount in grams of an aqueous solution, containing 0.9 weight percent sodium chloride, a gram of a material can absorb in about 10 hours under a load of about 0.3 pound per square inch (psi). As a general rule, it is desired that the absorbent composition of the present invention has an initial Absorbency Under Load value, for a load of about 0.3 psi, of at least about 15, beneficially of at least about 20, suitably of at least about 25, and up to about 100 grams per gram. As used herein, the term "initial Absorbency Under Load value" is meant to refer to that Absorbency Under Load value exhibited by a material as measured within about one day after preparation of the material while the material is stored at ambient conditions, such as at about 24° C. and between about 30 to about 60 percent relative humidity.

The absorbent composition of the present invention suitably has the ability to relatively slowly absorb a liquid. As used herein, the quantification of the rate with which any absorbent composition, either of the present invention or of those that are not of the present invention, absorbs a liquid will be referred to as the Time to Reach 60 Percent of Free Swell Capacity value. The method by which the Time to Reach 60 Percent of Free Swell Capacity value is determined is set forth below in connection with the examples. The Time to Reach 60 Percent of Free Swell Capacity values determined as set forth below and reported herein refer to the time, in minutes, that it takes an absorbent composition to absorb about 60 percent of the absorbent composition's total absorptive capacity, as represented by the absorbent composition's Free Swell value. As a general rule, it is desired that the absorbent composition of the present invention has a Time to Reach 60 Percent of Free Swell Capacity value of at least about 5 minutes, beneficially between about 5 minutes to about 300 minutes, more beneficially between about 10 minutes to about 200 minutes, suitably between about 20 minutes to about 100 minutes, and more suitably between about 30 minutes to about 60 minutes.

The absorbent composition of the present invention suitably also has the ability to relatively slowly absorb a liquid while the absorbent composition is under an external pressure or load. As used herein, the quantification of the rate with which any absorbent composition, either of the present invention or of those that are not of the present invention, absorbs a liquid while the absorbent composition is under an external pressure or load will be referred to as the Time to Reach 60 Percent of Absorbency Under Load Capacity value. The method by which the Time to Reach 60 Percent of Absorbency Under Load Capacity value is determined is set forth below in connection with the examples. The Time to Reach 60 Percent of Absorbency Under Load Capacity values determined as set forth below and reported herein refer to the time, in minutes, that it takes an absorbent composition to absorb about 60 percent of the absorbent composition's total absorptive capacity under an external pressure or load, as represented by the absorbent composition's Absorbency Under Load value. As a general rule, it is desired that the absorbent composition of the present invention has a Time to Reach 60 Percent of Absorbency Under Load Capacity value of at least about 5 minutes, beneficially between about 5 minutes to about 300 minutes, more beneficially between about 10 minutes to about 200 minutes, suitably between about 20 minutes to about 100 minutes, and more suitably between about 30 minutes to about 60 minutes.

It has been found that the absorbent composition of the present invention may be prepared by a simple process. In general, the method of making the absorbent composition comprises the step of mixing together the acidic or basic water-swellable, water-insoluble polymer, substantially in its free acid or free base form, respectively, with the basic second material or an acidic second material. As such, in one embodiment of the present invention, the absorbent composition will be prepared by mixing together an acidic water-swellable, water-insoluble polymer, substantially in its free acid form, and a basic second material. In another embodiment of the present invention, the absorbent composition will be prepared by mixing together a basic water-swellable, water-insoluble polymer, substantially in its free base form, and an acidic second material.

Such mixtures should generally be prepared under conditions that are sufficient for the acidic or basic water-swellable, water-insoluble polymer, substantially in its free acid or free base form, respectively, and the basic second material or an acidic second material to be effectively mixed together. Such mixtures will beneficially be agitated, stirred, or otherwise blended to effectively mix the polymer and the second material such that an essentially uniform mixture is formed. Equipment for achieving such agitation, stirring, or blending are well known in the art and include simple blenders and mixers.

While the principal components of the absorbent composition of the present invention have been described in the foregoing, such absorbent composition is not limited thereto and can include other components not adversely effecting the absorbent composition having the desired absorbent properties. Exemplary materials which could be used as additional components would include, without limitation, pigments, antioxidants, stabilizers, surfactants, waxes, flow promoters, solid solvents, particulates, and materials added to enhance processability of the absorbent composition.

The absorbent composition of the present invention is suitable for use in disposable absorbent products such as personal care products, such as diapers, training pants, baby wipes, feminine care products, adult incontinent products; and medical products, such as wound dressings or surgical capes or drapes. When the absorbent composition of the present invention is intended for use in disposable absorbent products, it is typically desired that the absorbent composition have a generally neutral or slightly acidic character. For such a particular use, it is generally desired that the molar ratio of acidic or basic water-swellable, water-insoluble polymer to basic or acidic second material be about 1 to 1.

In one embodiment of the present invention, a disposable absorbent product is provided, which disposable absorbent product comprises a liquid-permeable topsheet, a backsheet attached to the topsheet, and an absorbent structure positioned between the topsheet and the backsheet wherein the absorbent structure comprises the absorbent composition of the present invention, wherein the absorbent composition exhibits desired absorbent properties.

Disposable absorbent products, according to all aspects of the present invention, are generally subjected during use to multiple insults of a body liquid. Accordingly, the disposable absorbent products are desirably capable of absorbing multiple insults of body liquids in quantities to which the absorbent products and structures will be exposed during use. The insults are generally separated from one another by a period of time.

Those skilled in the art will recognize materials suitable for use as the topsheet and backsheet. Exemplary of materials suitable for use as the topsheet are liquid-permeable materials, such as spunbonded polypropylene or polyethylene having a basis weight of from about 15 to about 25 grams per square meter. Exemplary of materials suitable for use as the backsheet are liquid-impervious materials, such as polyolefin films, as well as vapor-pervious materials, such as microporous polyolefin films.

The absorbent composition is typically present in an absorbent structure in conjunction with a fibrous matrix. A fibrous matrix may take the form of, for example, a batt of comminuted wood pulp fluff, a tissue layer, a hydroentangled pulp sheet, or a mechanically softened pulp sheet. Suitably, the fibrous matrix is formed so as to constrain or entrap the absorbent composition within, or onto, its structure. The absorbent composition may be incorporated into or onto the fibrous matrix either during or after the formation of the general form of the fibrous matrix. A fibrous matrix useful in the present invention may be formed by an air-laying process or a wet-laid process, or by essentially any other process known to those skilled in the art for forming a fibrous matrix.

The absorbent composition is typically present in an absorbent structure or product of the present invention in an amount effective to result in the absorbent structure or product being able to absorb a desired amount of liquid. The absorbent composition is beneficially present in an absorbent structure in an amount of from about 1 to about 99 weight percent, suitably in an amount of from about 5 to about 95 weight percent, and more suitably of from about 10 to about 90 weight percent, based on the total weight of the absorbent composition and a substrate in the absorbent structure.

Test Methods

Free Swell Capacity and Time to Reach 60 Percent of Free Swell Capacity

The Free Swell Capacity (FS) is a test which measures the amount in grams of an aqueous solution, containing 0.9 weight percent sodium chloride, a gram of a material can absorb in 10 hours under a negligible applied load or restraining force, such as of about 0.01 pound per square inch.

Figure 1:
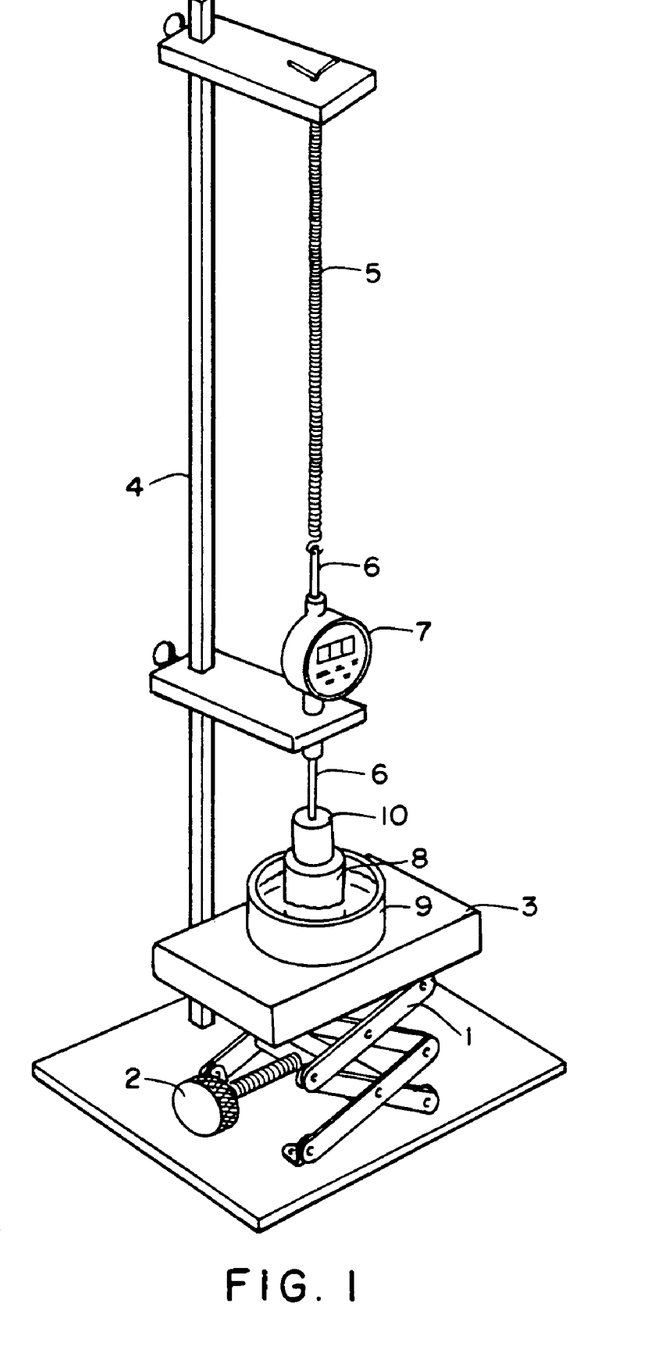
FIG. 1 is an illustration of the equipment employed in determining the Free Swell and Absorbency Under Load values of an absorbent composition.

Referring to FIG. 1, the apparatus and method for determining the Free Swell and the Absorbency Under Load will be described. Shown is a perspective view of the apparatus in position during a test. Shown is a laboratory jack 1 having an adjustable knob 2 for raising and lowering the platform 3. A laboratory stand 4 supports a spring 5 connected to a modified thickness meter probe 6, which passes through the housing 7 of the meter, which is rigidly supported by the laboratory stand. A plastic sample cup 8, which contains the superabsorbent material sample to be tested, has a liquid-permeable bottom and rests within a Petri dish 9 which contains the saline solution to be absorbed. For the determination of Absorbency Under Load values only, a weight 10 rests on top of a spacer disc (not visible) resting on top of the superabsorbent material sample (not visible).

The sample cup consists of a plastic cylinder having a 1 inch inside diameter and an outside diameter of 1.25 inches. The bottom of the sample cup is formed by adhering a 100 mesh metal screen having 150 micron openings to the end of the cylinder by heating the screen above the melting point of the plastic and pressing the plastic cylinder against the hot screen to melt the plastic and bond the screen to the plastic cylinder.

The modified thickness meter used to measure the expansion of the sample while absorbing the saline solution is a Mitutoyo Digimatic Indicator, IDC Series 543, Model 543-180, having a range of 0–0.5 inch and an accuracy of 0.00005 inch (Mitutoyo Corporation, 31-19, Shiba 5-chome, Minato-ku, Tokyo 108, Japan). As supplied from Mitutoyo Corporation, the thickness meter contains a spring attached to the probe within the meter housing. This spring is removed to provide a free-falling probe which has a downward force of about 27 grams. In addition, the cap over the top of the probe, located on the top of the meter housing, is also removed to enable attachment of the probe to the suspension spring 5 (available from McMaster-Carr Supply Co., Chicago, Ill., Item No. 9640K41), which serves to counter or reduce the downward force of the probe to about 1 gram±0.5 gram. A wire hook can be glued to the top of the probe for attachment to the suspension spring. The bottom tip of the probe is also provided with an extension needle (Mitutoyo Corporation, Part No. 131279) to enable the probe to be inserted into the sample cup.

To carry out the test, a 0.160 gram sample of an absorbent material sample, which has typically been sieved to a particle size between 300 and 600 microns, is placed into the sample cup. The sample is then covered with a plastic spacer disc, weighing 4.4 grams and having a diameter of about 0.995 inch, which serves to protect the sample from being disturbed during the test and also to uniformly apply a load on the entire sample. The sample cup, with material sample and spacer disc, is then weighed to obtain its dry weight. The sample cup is placed in the Petri dish on the platform and the laboratory jack raised up until the top side of the plastic spacer disc contacts the tip of the probe. The meter is zeroed. A sufficient amount of saline solution is added to the Petri dish (50–100 milliliters) to begin the test. The distance the plastic spacer disc is raised by the expanding sample as it absorbs the saline solution is measured by the probe. This distance, multiplied by the cross-sectional area inside the sample cup, is a measure of the expansion volume of the sample due to absorption. Factoring in the density of the saline solution and the weight of the sample, the amount of saline solution absorbed is readily calculated. The weight of saline solution absorbed after about 10 hours is the Free Swell value expressed as grams saline solution absorbed per gram of absorbent. If desired, the readings of the modified thickness meter can be continuously inputted to a computer (Mitutoyo Digimatic Miniprocessor DP-2 DX) to make the calculations and provide Free Swell readings. As a cross-check, the Free Swell can also be determined by determining the weight difference between the sample cup before and after the test, the weight difference being the amount of solution absorbed by the sample.

From the continuous monitoring of the Free Swell values provided by the computer, the Time to Reach 60 Percent of Free Swell Capacity is readily determined.

Absorbency under Load Capacity and Time to Reach 60 Percent of Absorbency under Load Capacity The Absorbency Under Load (AUL) is a test which measures the amount in grams of an aqueous solution, containing 0.9 weight percent sodium chloride, a gram of a material can absorb in 10 hours under an applied load or restraining force of about 0.3 pound per square inch. The procedure for measuring the Absorbency Under Load value of an absorbent composition is essentially identical to the procedure for measuring the Free Swell values, except that a 100 gram weight is placed on top of the plastic spacer disc, thereby applying a load of about 0.3 pound per square inch onto the absorbent composition as it absorbs the saline solution. From the continuous monitoring of the Absorbency Under Load values provided by the computer, the Time to Reach 60 Percent of Absorbency Under Load Capacity is readily determined.

EXAMPLES

For use in the following examples, the following sample materials were prepared. The description and properties of these samples are summarized in Table 1.

a. Commercial Polyacrylate Superabsorbent (Sample 1)

As a control material, a commercial polyacrylate superabsorbent, designated as IM 3900, was obtained from Hoechst Celanese. The superabsorbent has a degree of neutralization of about 70 mole percent.

b. Polyacrylic Acid Gel (Sample 2 to Sample 5)

Into a 500 ml flask which contains 175 grams of distilled water, 27 grams of acrylic acid, 0.065 gram of potassium persulfate ($K_2S_2O_8$), and 0.108 gram of N,N'-methylene bisacrylamide, all available from Aldrich Chemical Company, were added and mixed at room temperature to form a completely dissolved solution. The flask was then immersed into a water bath at 60° C. for at least three hours. The flask was shaken continuously. The polyacrylic acid gel formed was cut and dried in a ventilated oven at 80° C. for 10 hours. The completely dried polymer was ground into particulate by a commercial blender from Warring (Model 34BL97) and sieved into different particle size ranges.

c. Polyacrylic Acid Gel with Different Degree of Neutralization (Sample 6 to Sample 8)

The particulate polyacrylic acid gel described in section b above was neutralized by mixing 300 to 600 micron polyacrylic acid gel with 0.1 weight percent sodium hydroxide aqueous solution. Degree of neutralization is controlled by the ratio of the polymer gel to the sodium hydroxide solution. The swollen gel was dried in ambient condition (23° C., 30 percent relative humidity) for at least three days before absorbency test.

d. Polyacrylic Acid with Different Molecular Weights (Sample 9 to Sample 11)

Three different molecular weight, linear polyacrylic acid prepolymers were purchased from Polysciences, Inc. The weight average molecular weights of the polyacrylic acids are 60,000, 240,000, and 4,000,000, respectively. The polyacrylic acids were each dissolved into a 2 percent aqueous solution in a mixer manufactured by KitchAid (Model K45SS) and 3 percent polyethylene oxide-polypropylene oxide copolymer (based on dry weight of the polyacrylic acid) was added into the solution. The polyethylene oxide-polypropylene oxide copolymer is from Polysciences, Inc. which has a molecular weight of about 3,000 and a molar ratio of ethylene oxid to propylene oxide about 0.8 to 1. The solution was stirred for at least 30 minutes and then dried in a 60° C. oven. The dried polymer was then ground and sieved into 300 to 600 micron particles, heated at 200° C. for about 20 minutes, and subjected to absorbing rate and absorbency evaluation.

e. Chitosan (Sample 12)

Twenty grams of chitosan flake available from Vanson were mixed with 1000 grams of 1 weight percent acetic acid solution in a mixer manufactured by KitchAid (Model K45SS). The solution was then dried at 60° C. for at least 20 hours and ground into particulate with a particle size ranging from 300 to 600 microns. The chitosan acetate particles were suspended in a 1 weight percent sodium hydroxide solution with a ratio of 1 gram of chitosan acetate to 100 grams of the sodium hydroxide solution. Under continuous stirring, using a magnetic stirrer, the chitosan acetate was converted into chitosan within at least 5 hours. The treated chitosan particles were then washed with distilled water four times with a ratio of chitosan to water 1 to 1000 to completely remove residual sodium acetate. The washed chitosan was dried at 80° C.

f. Polyacrylamido Methylpropane Sulfonic Acid (Sample 13)

Ten grams of acrylamidomethylpropanesulfonic acid monomer was dissolved in 40 grams distilled water in a 100 ml conical flask. To this solution 0.5 gram of methylenebisacrylamide was added as the crosslinking agent and dissolved. The solution was purged with nitrogen for 15 minutes and the conical flask was stoppered and placed in a water bath maintained at 60° C. Polymerization was initiated by adding 0.04 gram of potassium persulfate and 0.015 gram of sodium bisulfite to the reaction mixture. Polymerization was continued for 12 hours at 60° C., followed by cutting the gel obtained into about one inch cubes and washing it in distilled water. The washed gel was dried at 50° C. overnight and ground using a commercial blender manufactured by Warring (Model 34BL97). The polymer after grinding was sieved and particles in the size range of 300 to 600 microns was collected for absorbency measurements.

g. Polydiallyl Dimethyl Ammonium Hydroxide (Sample 14)

About 0.21 grams of methylenebisacrylamide was dissolved as the crosslinking agent in 37 milliliters of 60 percent by weight aqueous solution of diallyldimethylammonium chloride monomer in a 100 milliliters conical flask. The solution was purged with nitrogen for 15 minutes and the conical flask was stoppered and placed in a water bath at 60° C. Polymerization was initiated by the addition of 0.04 gram of potassium persulfate and 0.15 gram of sodium bisulfite to the reaction mixture. Polymerization was continued for 12 hours at 60° C. followed by cutting the gel that was formed into small pieces (about one inch cubes). The gel pieces were washed with 2 percent by weight sodium hydroxide solution until all the chloride ions in the polymer were exchanged for hydroxide ions. The completion of exchange was confirmed by testing the effluent after treatment with acidified silver nitrate to detect for chloride ions. The absence of chloride ions was taken as an indication of completion of conversion to hydroxide form. The gel was washed thoroughly with distilled water until the pH of the distilled water after washing was the same as the water used for washing. The gel was dried at 50° C. overnight and ground using a blender from Warring (Model 34BL97). The polymer after grinding was sieved and particles in the size range of 300 to 600 microns was collected for absorbency measurements.

TABLE 1

| Sample No. | Description | Molecular Weight | Particle Size | D.N.[a] |
|---|---|---|---|---|
| Sample 1 | Na-polyacrylate | NA | 300–600 μm | 70% |
| Sample 2 | polyacrylic acid | NA | 150–300 μm | 0% |
| Sample 3 | polyacrylic acid | NA | 300–600 μm | 0% |
| Sample 4 | polyacrylic acid | NA | 600–850 μm | 0% |
| Sample 5 | polyacrylic acid | NA | >850 μm | 0% |
| Sample 6 | Na-polyacrylate | NA | 600–850 μm | 10% |
| Sample 7 | Na-polyacrylate | NA | 600–850 μm | 20% |
| Sample 8 | Na-polyacrylate | NA | 600–850 μm | 30% |
| Sample 9 | polyacrylic acid | 4,000,000 | 300–600 μm | 0% |
| Sample 10 | polyacrylic acid | 240,000 | 300–600 μm | 0% |
| Sample 11 | polyacrylic acid | 60,000 | 300–600 μm | 0% |
| Sample 12 | chitosan | 11,000 cps[b] | 300–600 μm | 0% |
| Sample 13 | polyacrylamide methylpropane sulfonic acid | NA | 300–600 μm | 0% |
| Sample 14 | polydiallyl dimethyl ammonium hydroxide | NA | 300–600 μm | 0% |

Note:
[a]Degree of Neutralization (0% means either 100% acid form or 100% base form)
[b]Viscosity of a 1% chitosan solution dissolved in a 1% acetic acid solution at 25° C.

Example 1

About 0.16 g of polyacrylic acid gel, chitosan, polyacrylamido methylpropane sulfonic acid, or polydiallyl dimethyl ammonium hydroxide, each with a particle size ranging from 300 to 600 microns, was separately weighed and placed into a testing cylinder to test its absorbing rate and total absorbency. Also, 0.16 g of mixtures of various polymers with the same particle size range and a molar ratio of one to one of the two respective polymers was weighed and placed into a testing cylinder to test absorbing rate and total absorbency of the mixtures. The results of the testing are listed in Table 2. The $pK_a$ value for Sample 3 represents the $pK_a$ for acrylic acid. The $pK_a$ value for Sample 13 represents the $pK_a$ for acrylamidomethylpropanesulfonic acid. The $pK_b$ value for Sample 14 represents the $pK_b$ for diallyldimethylammonium chloride.

TABLE 2

| Material(s) Used | $pK_a$[a] | $pK_b$[a] | Molar Ratio (acid/base) | Time to Reach 60% of Free Swell Capacity | Free Swell Capacity |
|---|---|---|---|---|---|
| *Sample 3 | 4.25 | | 1/0 | 7 min | 8.5 g/g |
| *Sample 12 | | 5–7 | 0/1 | 9 min | 3.4 g/g |
| *Sample 13 | <1 | | 1/0 | 2 min | 25.2 g/g |
| *Sample 14 | | <1 | 0/1 | 4 min | 26.0 g/g |
| Sample 3/12 | 4.25 | 5–7 | 1/1 | 60 min | 30.2 g/g |
| *Sample 13/12 | <1 | 5–7 | 1/1 | 3 min | 28.5 g/g |
| *Sample 3/14 | 4.25 | <1 | 1/1 | 2 min | 42.0 g/g |
| *Sample 13/14 | <1 | <1 | 1/1 | 2 min | 31.4 g/g |

Note:
[a]Values obtained from Friedrich Helfferich, Ion Exchange, page 84, MaGraw-Hill Book Company, 1962.
*Not an example of the present invention.

Example 2

About 0.16 gram of polyacrylic acid gel, chitosan, commercial polyacrylate gel or mixtures of polyacrylic acid (with different particle size distribution) and chitosan were weighed and placed into a testing cylinder to test its absorbing rate and total absorbency. The Table 3 summarizes the results obtained.

TABLE 3

| Material(s) Used | Particle Size | Molar Ratio | Time to Reach 60% of Total Capacity | Free Swell Capacity |
|---|---|---|---|---|
| *Sample 1 | 300–600 μm | NA | 3 min | 41.2 g/g |
| *Sample 3 | 300–600 μm | NA | 7 min | 8.5 g/g |
| *Sample 12 | 300–600 μm | NA | 9 min | 3.4 g/g |
| Sample 2/12 | 150–300 μm | 1/1 | 40 min | 24.9 g/g |
| Sample 3/12 | 300–600 μm | 1/1 | 60 min | 30.2 g/g |
| Sample 4/12 | 600–850 μm | 1/1 | 100 min | 25.4 g/g |
| Sample 5/12 | >850 μm | 1/1 | 160 min | 16.5 g/g |

*Not an example of the present invention.

Example 3

Either water insoluble polymer gel or water soluble material was selected as the second basic material and mixed with acidic polyacrylic acid gel to evaluate the absorbing rate and total absorbency. Table 4 lists the results obtained. The sodium hydroxide used (NaOH) is pre-dissolved into 0.9 weight percent sodium chloride solution. The $NaHCO_3$ or the NaCitrate is mixed directly with the acidic polyacrylic acid gel. The NaCitrate represents citric acid trisodium salt. The $pK_a$ value for Sample 3 represents the $pK_a$ for acrylic acid. The $pK_a$ value for Sample 14 represents the $pK_b$ for diallyldimethylammonium chloride.

TABLE 4

| Material(s) Used | $pK_a$ | $pK_b$ | Molar Ratio | Time to Reach 60% Total Capacity | Free Swell Capacity |
|---|---|---|---|---|---|
| *Sample 3 | 4.25 | — | NA | 7 min | 8.5 g/g |
| Sample 3/12 | 4.25 | 5–7 | 1/1 | 60 min | 30.2 g/g |
| *Sample 3/14 | 4.25 | <1 | 1/1 | 2 min | 42.0 g/g |
| Sample 3/ NaOH | 4.25 | <1 | 1.5/1 | 15 min | 16.0 g/g |
| Sample 3/ NaOH | 4.25 | <1 | 1/1.1 | 10 min | 22.2 g/g |
| Sample 3/ NaOH | 4.25 | <1 | 1/1.4 | 40 min | 33.2 g/g |
| Sample-3/ $NaHCO_3$ | 4.25 | >2 | 1/1 | 30 min | 19.4 g/g |
| Sample-3/ NaCitrate | 4.25 | >2 | 1/1 | 30 min | 19.3 g/g |

*Not an example of the present invention.

Example 4

The ratio of acidic polymer gel to basic second polymer was changed and the absorbency tests of corresponding mixtures were evaluated. The results are listed in Table 5.

TABLE 5

| Material(s) Used | Molar Ratio (PA/Chitosan) | Time to Reach 60% of Free Swell Capacity | Free Swell Capacity |
|---|---|---|---|
| *Sample 3/12 | 0.25/1 | 60 min | 12.3 g/g |
| Sample 3/12 | 0.5/1 | 110 min | 22.7 g/g |

TABLE 5-continued

| Material(s) Used | Molar Ratio (PA/Chitosan) | Time to Reach 60% of Free Swell Capacity | Free Swell Capacity |
|---|---|---|---|
| Sample 3/12 | 1/1 | 60 min | 30.2 g/g |
| Sample 3/12 | 1/0.73 | 70 min | 24.4 g/g |
| Sample 3/12 | 1/0.26 | 80 min | 22.0 g/g |

*Not an example of the present invention.

Example 5

Polyacrylic acid gel prepared from linear polyacrylic acids with different molecular weights was mixed with basic chitosan material with a molar ratio of 1 to 1. Fluid absorbing rate and total absorbency values of such mixtures were evaluated and the results are listed in Table 6.

TABLE 6

| Material(s) Used | Mw of PA | Molar Ratio (PA/Chitosan) | Time to Reach 60% of Total Capacity | Free Swell Capacity |
|---|---|---|---|---|
| Sample 9/12 | 4,000,000 | 1/1 | 90 min | 38.7 g/g |
| Sample 10/12 | 240,000 | 1/1 | 70 min | 20.4 g/g |
| *Sample 11/12 | 60,000 | 1/1 | 80 min | 12.0 g/g |

*Not an example of the present invention

Example 6

Polyacrylic acid gels, with different degrees of neutralization ranging from 0 percent to 30 percent, were mixed with basic chitosan material and subjected to the absorbency tests. The results are summarized in Table 7. In Table 7, D.N. stands for degree of neutralization in molar percentage.

TABLE 7

| Material(s) Used | D.N. (%) | Molar Ratio (PA/Chitosan) | Time to Reach 60% of Free Swell Capacity | Free Swell Capacity |
|---|---|---|---|---|
| Sample 4/12 | 0 | 1/1 | 100 min | 19.6 g/g |
| Sample 6/12 | 10 | 1/1 | 150 min | 22.7 g/g |
| Sample 7/12 | 20 | 1/1 | 50 min | 19.7 g/g |
| Sample 8/12 | 30 | 1/1 | 50 min | 15.7 g/g |

Example 7

Polyacrylic acid/chitosan mixtures were evaluated for Absorbency Under Load (AUL) values. The results are listed in Table 8.

TABLE 8

| Material(s) Used | Particle Size of PA | Molar Ratio (PA/Chitosan) | Time to Reach 60% of AUL Capacity | AUL at 10 hrs |
|---|---|---|---|---|
| *Sample 1 | 300–600 μm | NA | 15 min | 29.8 g/g |
| *Sample 3 | 300–600 μm | NA | 15 min | 5.6 g/g |
| *Sample 12 | 300–600 μm | NA | 7 min | 2.3 g/g |
| Sample 3/12 | 300–600 μm | 1/1 | 100 min | 21.5 g/g |
| Sample 4/12 | 600–850 μm | 1/1 | 120 min | 16.3 g/g |
| Sample 5/12 | >850 μm | 1/1 | 180 min | 13.6 g/g |

*Not an example of the present invention.

While the present invention has been described in terms of the specific embodiments described above, numerous equivalent changes and modifications will be clear to those skilled in the art. Accordingly, the specific examples set forth above are not intended to limit in any manner the scope of the invention as set forth in the appended claims.

What is claimed is:

1. An absorbent composition comprising a mixture of:
   a) an acidic water-swellable, water-insoluble polymer having a pKa between about 2 and about 12 wherein the acidic water-swellable, water-insoluble polymer comprises acidic functional groups and has at least about 50 molar percent of the acidic functional groups in free acid form; and
   b) a basic material;
   wherein the absorbent composition exhibits a Free Swell value that is at least about 15 grams per gram of absorbent composition and a Time to Reach 60 Percent of Free Swell Capacity value of at least about 5 minutes and wherein the mixture is not a molecular level dispersion of the acidic water-swellable, water-insoluble polymer and the basic material.

2. The absorbent composition of claim 1 wherein the acidic water-swellable, water-insoluble polymer has a pK$_a$ between about 2 and 10.

3. The absorbent composition of claim 1 wherein the acidic water-swellable, water-insoluble polymer has at least about 70 molar percent of the acidic functional groups in free acid form.

4. The absorbent composition of claim 1 wherein the acidic water-swellable, water-insoluble polymer has a weight average molecular weight greater than about 100,000.

5. The absorbent composition of claim 4 wherein the acidic water-swellable, water-insoluble polymer has a weight average molecular weight greater than about 200,000.

6. The absorbent composition of claim 1 wherein the acidic water-swellable, water-insoluble polymer is prepared from a base polymer selected from the group consisting of polyacrylamides, polyvinyl alcohols, ethylene maleic anhydride copolymer, polyvinylethers, polyacrylic acids, polyvinylpyrrolidones, polyvinylmorpholines, carboxymethyl celluloses, carboxymethyl starches, hydroxypropyl celluloses, algins, alginates, carrageenans, acrylic grafted starches, acrylic grafted celluloses, polyaspartic add, polyglutamic acid, and copolymers comprising at least two of the preceding polymers.

7. The absorbent composition of claim 1 wherein the basic material is selected from the group consisting of polyamines, polyimines, polyamides, polyquaternary ammoniums, chitins, chitosans, polyasparagins, polyglutamines, polylysines, polyarginines, organic salts, aliphatic amines, aromatic amines, imines, amides, metallic oxides, hydroxides, salts, and mixtures thereof.

8. The absorbent composition of claim 1 wherein the basic material is a water-swellable, water-insoluble polymer.

9. The absorbent composition of claim 8 wherein the water-swellable, water-insoluble polymer basic material has a pK$_b$ between about 2 and 12.

10. The absorbent composition of claim 1 wherein the acidic water-swellable, water-insoluble polymer and the basic material are present in the absorbent composition in a molar ratio between about 10:1 and 1:10.

11. The absorbent composition of claim 1 wherein the absorbent composition has a Free Swell value of at least about 20 grams per gram of absorbent composition.

12. The absorbent composition of claim 1 wherein the absorbent composition has a Time to Reach 60 Percent of Free Swell Capacity value of between about 10 minutes and 200 minutes.

13. The absorbent composition of claim 1 wherein the absorbent composition has an Absorbency Under Load value of at least about 15.

14. The absorbent composition of claim 1 wherein the absorbent composition has a Time to Reach 60 Percent of Absorbency Under Load Capacity value of at least about 5 minutes.

15. The absorbent composition of claim 1 wherein the water-swellable, water-insoluble polymer comprises acidic functional groups and has at least about 50 molar percent of the acidic functional groups in free acid form, has a weight average molecular weight greater than about 100,000, and the acidic water-swellable, water-insoluble polymer and the basic material are present in the absorbent composition in a molar ratio between about 10:1 and 1:10.

16. A disposable absorbent product comprising a liquid-permeable topsheet, a backsheet attached to the topsheet, and an absorbent structure positioned between the topsheet and the backsheet wherein the absorbent structure comprises an absorbent composition comprising:

a) an acidic water-swellable, water-insoluble polymer having a $pK_a$ between about 2 and about 12 wherein the acidic water-swellable, water-insoluble polymer comprises acidic functional groups and has at least about 50 molar percent of the acidic functional groups in free acid form; and b) a basic material;

wherein the absorbent composition exhibits a Free Swell value that is at least about 15 grams per gram of absorbent composition and a Time to Reach 60 Percent of Free Swell Capacity value of at least about 5 minutes and wherein the absorbent composition is not a molecular level dispersion of the acidic water-swellable, water-insoluble polymer and the basic material.

* * * * *